United States Patent [19]

Ueda

[11] Patent Number: 5,314,775
[45] Date of Patent: May 24, 1994

[54] PHOTOSENSITIVE MEMBER COMPRISING A DIAMINO COMPOUND

[75] Inventor: Hideaki Ueda, Kawanishi, Japan

[73] Assignee: Minolta Camera Kabushiki Kaisha, Osaka, Japan

[21] Appl. No.: 926,284

[22] Filed: Aug. 10, 1992

[30] Foreign Application Priority Data

Aug. 15, 1991 [JP] Japan .................................. 3-205203

[51] Int. Cl.$^5$ .................................................. G03G 5/04
[52] U.S. Cl. .................................... 430/59; 430/73; 430/74
[58] Field of Search ............................... 430/59, 73, 74

[56] References Cited

U.S. PATENT DOCUMENTS

| | | | |
|---|---|---|---|
| 4,127,412 | 11/1978 | Rule et al. | 96/1 PC |
| 4,297,425 | 10/1981 | Pai et al. | 430/58 |
| 4,898,800 | 2/1990 | Shimada et al. | 430/59 |
| 4,920,022 | 4/1990 | Sakakibara et al. | 430/59 |
| 4,931,371 | 6/1990 | Matsumoto et al. | 430/59 |
| 4,937,165 | 6/1990 | Ong et al. | 430/59 |
| 4,948,689 | 8/1990 | Kuroda et al. | 430/59 |
| 4,988,595 | 1/1991 | Pai et al. | 430/59 |

FOREIGN PATENT DOCUMENTS

0004242 1/1977 Japan .
2-190864 1/1989 Japan .

*Primary Examiner*—Marion E. McCamish
*Assistant Examiner*—Rosemary Ashton
*Attorney, Agent, or Firm*—Burns, Doane, Swecker & Mathis

[57] ABSTRACT

The present invention provides a new diamino compound represented by the following general formula [I].

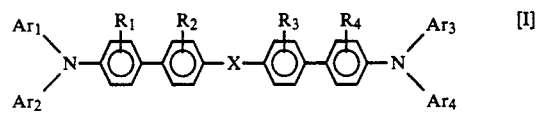

The present invention provides also a photosensitive member and an electroluminescence device both of which comprise the diamino compound of the general formula [I] as a charge transporting material.

9 Claims, 2 Drawing Sheets

PHOTOSENSITIVE MEMBER COMPRISING A DIAMINO COMPOUND

BACKGROUND OF THE INVENTION

The present invention relates to a new compound with a diamino structure. The amino compound is used as a photosensitive material. In particular, the diamino compound can be applied to a photosensitive member or an electroluminescence device as a charge transporting material.

Many organic compounds such as anthracenes, anthraquinones, imidazoles, carbazoles and styryl derivatives, which can be used as a photosensitive material or a charge transporting material, have been known.

However, when the materials described above are applied, for example, to a photosensitive member, compatibility with other members, durability and weathering resistance are required basically as well as good photosensitivity and good charge transportability. The fact is that there are few materials meeting such characteristics as above mentioned.

SUMMARY OF THE INVENTION

The object of the present invention is to provide a new diamino compound.

Another object of the present invention is to provide a photosensitive member containing the new diamino compound.

Another object of the present invention is to provide an electroluminescence device having a charge transporting layer composed of the new amino compound.

The present invention relates to a photosensitive member having a photosensitive layer on an electrically conductive substrate, characterized by that the photosensitive layer comprises a diamino compound represented by the following general formula [I]:

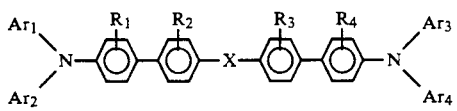

in which $Ar_1$, $Ar_2$, $Ar_3$ and $Ar_4$ represent respectively an alkyl group, an aralkyl group, an aryl group, a biphenyl group or a heterocyclic group, each of which may have a substituent; $R_1$, $R_2$, $R_3$ and $R_4$ represent respectively a hydrogen atom, an alkyl group, an alkoxy group or a halogen atom; X represents —O—, —S— or

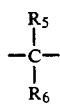

in which $R_5$ and $R_6$ represent respectively a hydrogen atom, an alkyl group or an aryl group.

The diamino compound is applied to a photosensitive member or an electroluminescence device.

DETAILED DESCRIPTION OF THE INVENTION

Figure 1:
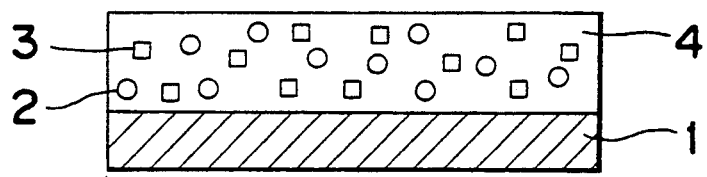
FIG. 1 is a schematic sectional view of a dispersion-type photosensitive member having a photosensitive layer on an electrically conductive substrate.

The present invention relates to a diamino compound represented by the following general formula [I]:

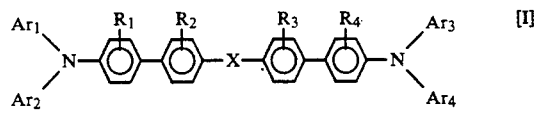

In the general formula [I], $Ar_1$, $Ar_2$, $Ar_3$ and $Ar_4$ represent respectively an alkyl group such as methyl and ethyl, an aralkyl group such as benzyl and phenethyl, an aryl group such as phenyl and tolyl, a biphenyl group or a heterocyclic group such as thionyl and furyl. The aryl group or the biphenyl group is preferable. $Ar_1$, $Ar_2$, $Ar_3$ and $Ar_4$ may have a substituent exemplified by an alkyl group (methyl and the like), an alkoxy (methoxy and the like), a phenoxy group and a halogen atom. Particularly preferable $Ar_1$, $Ar_2$, $Ar_3$ and $Ar_4$ are phenyl and biphenyl each of has an alkyl group.

$R_1$, $R_2$, $R_3$ and $R_4$ represent respectively a hydrogen atom, an alkyl group such as methyl and ethyl, an alkoxy group such as methoxy and ethoxy or a halogen atom such as chlorine atom and bromine atom.

X represents —O—, —S— or

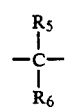

in which $R_5$ and $R_6$ represent respectively a hydrogen atom, an alkyl group such as methyl and ethyl or an aryl group such as phenyl and tolyl.

Concrete compounds having the diamino structure represented by the general formula [I] are exemplified as shown below:

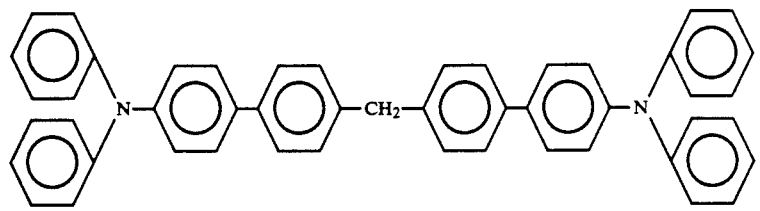
[1]
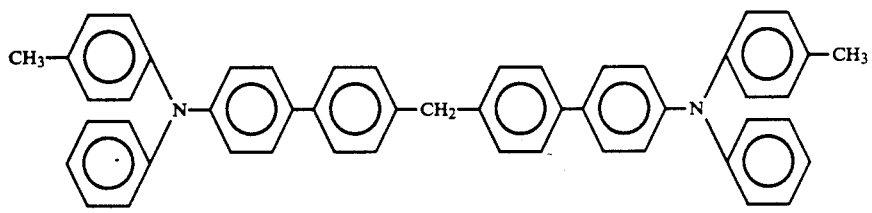
[2]
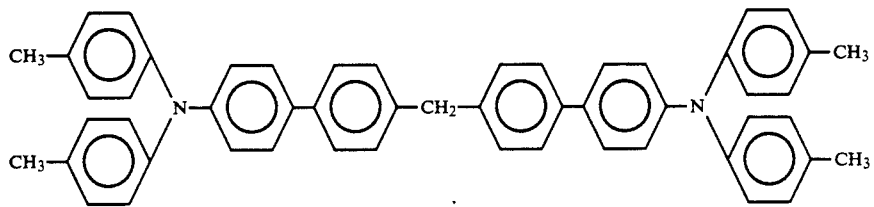
[3]
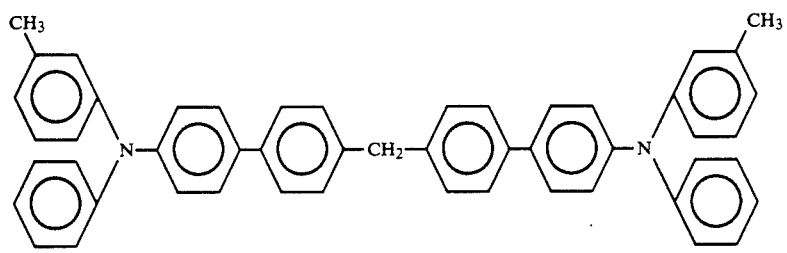
[4]
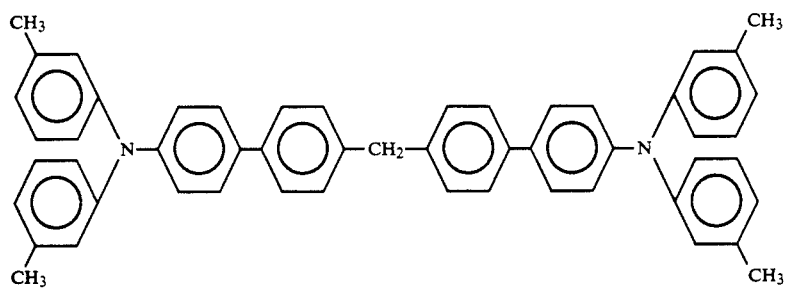
[5]
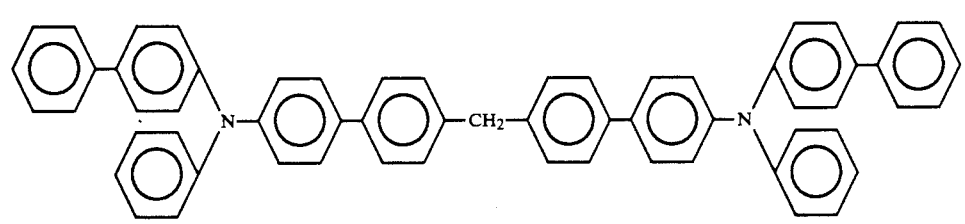
[6]
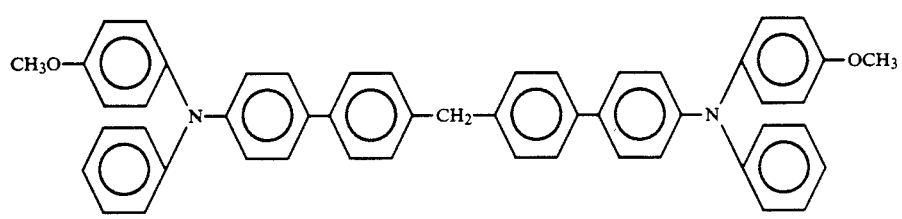
[7]

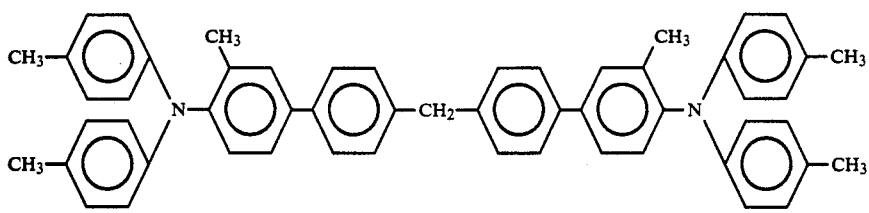
[8]
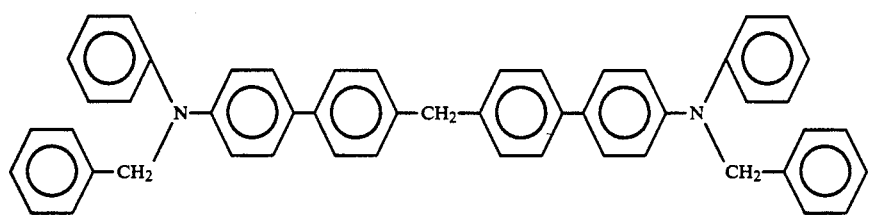
[9]
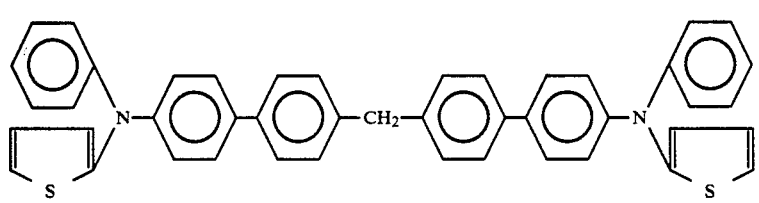
[10]
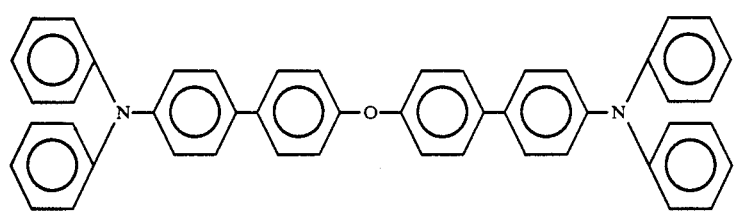
[11]
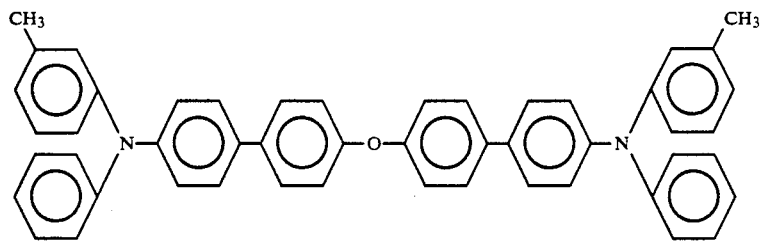
[12]
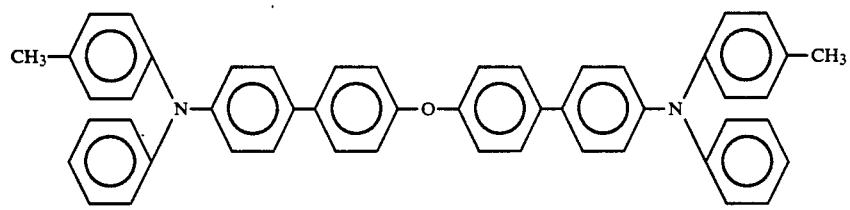
[13]
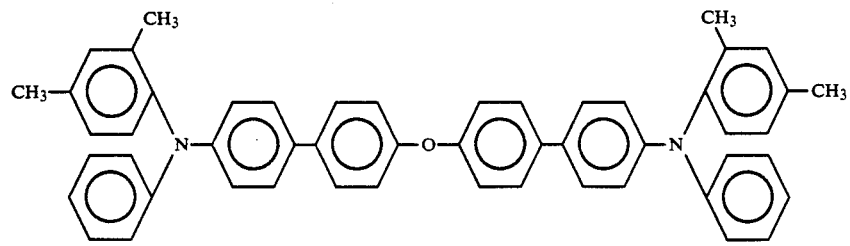
[14]

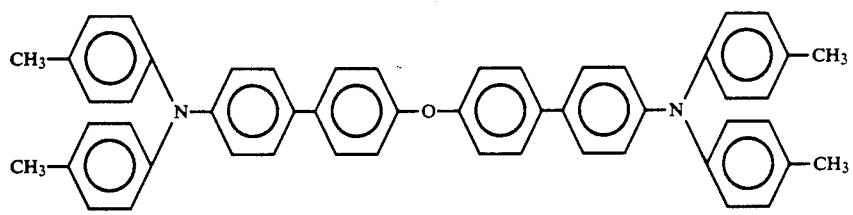
[15]
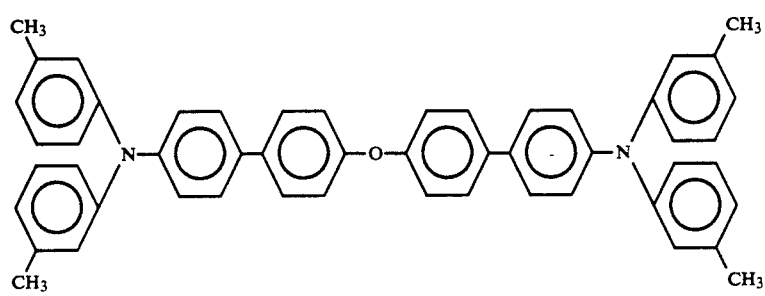
[16]
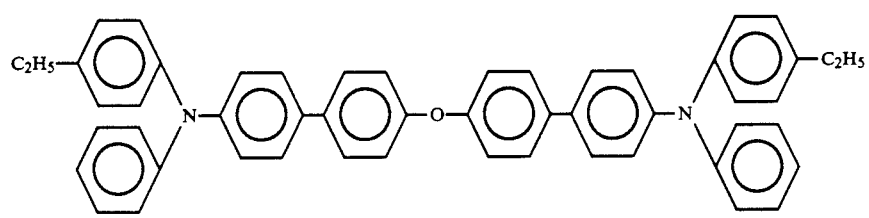
[17]
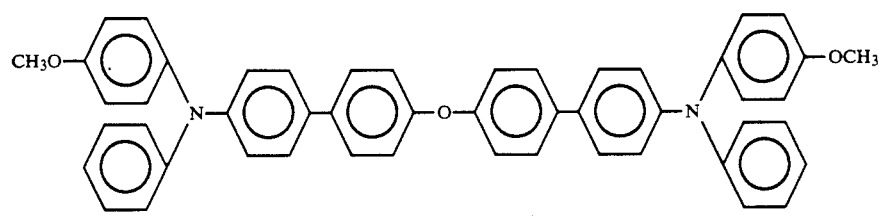
[18]
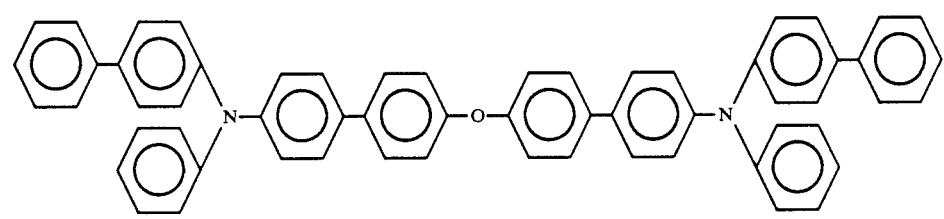
[19]
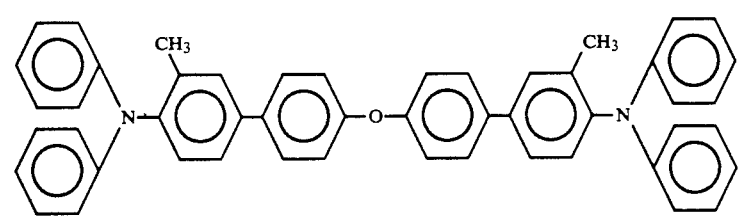
[20]
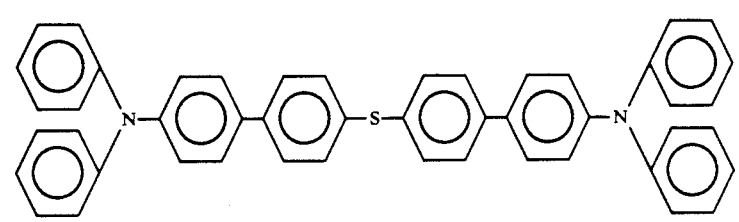
[21]

-continued
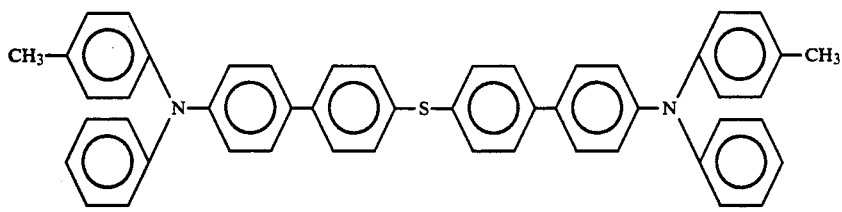 [22]
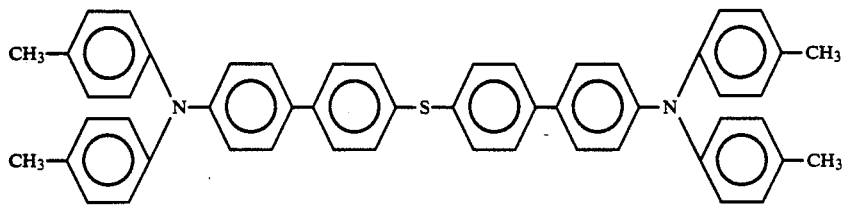 [23]
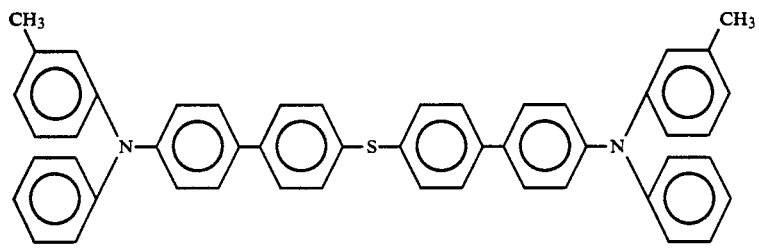 [24]
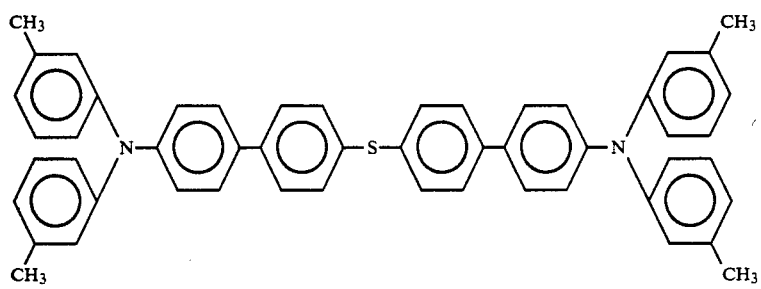 [25]
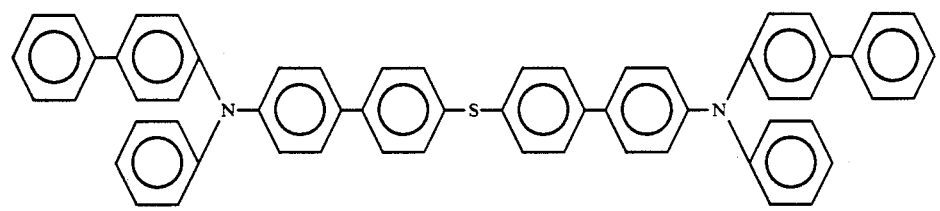 [26]
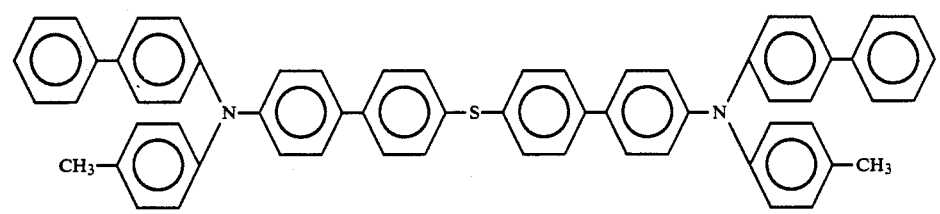 [27]
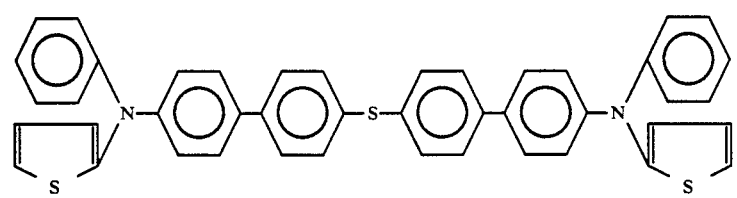 [28]

-continued
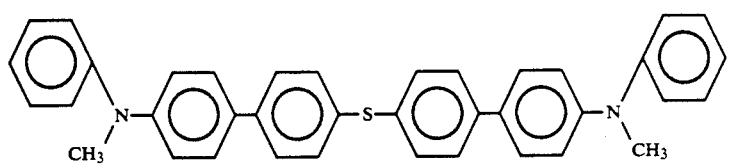
[29]
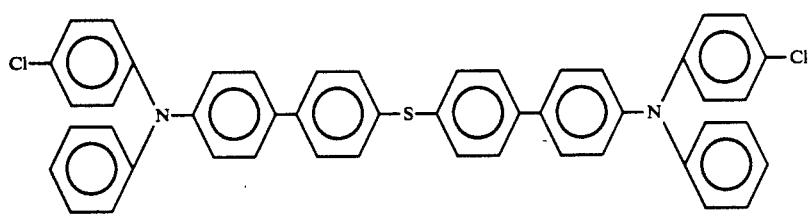
[30]
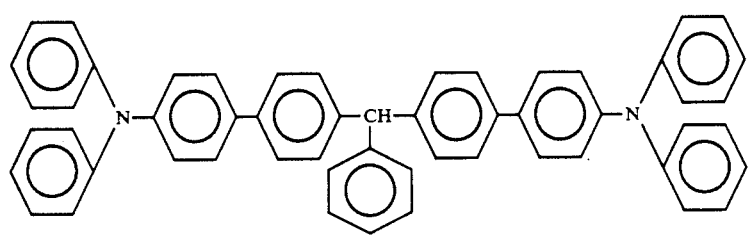
[31]
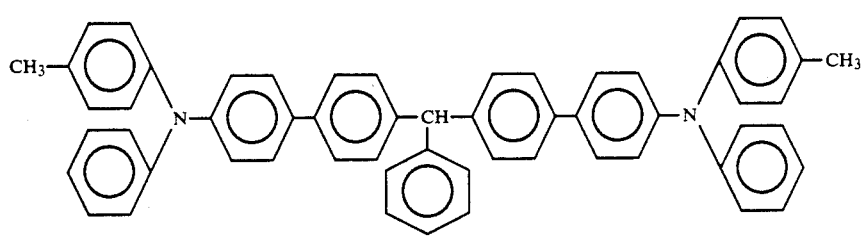
[32]
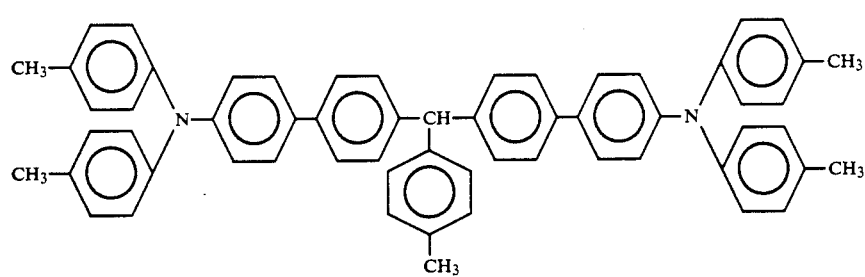
[33]
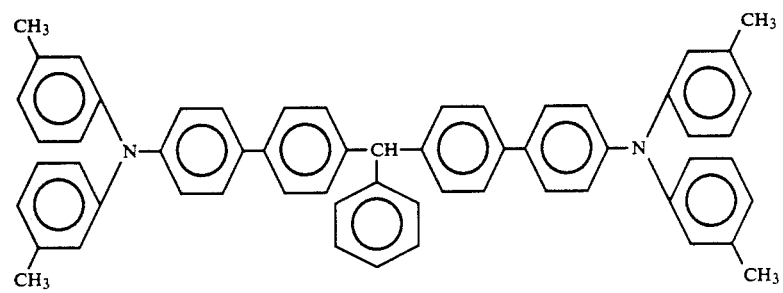
[34]

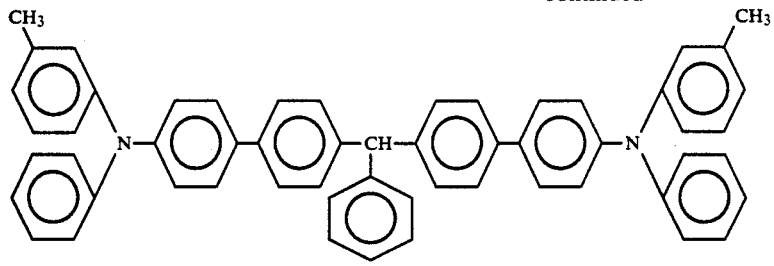
[35]
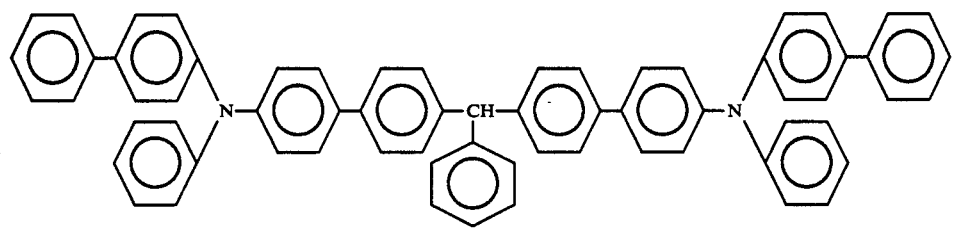
[36]
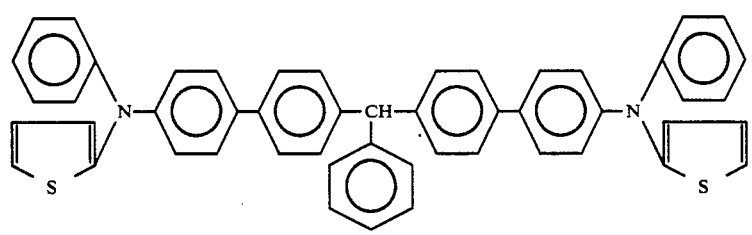
[37]
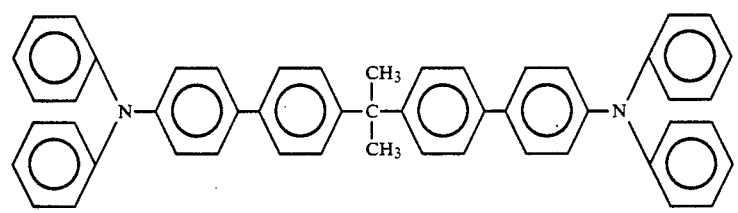
[38]
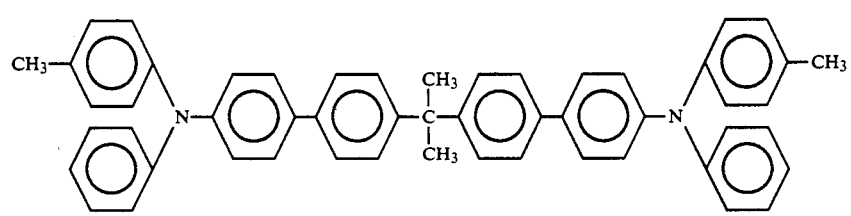
[39]
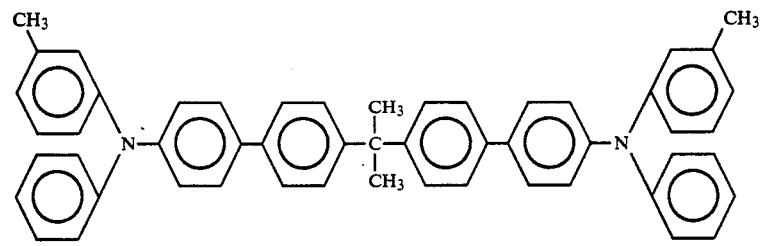
[40]
A diamino compound represented by the general formula [I] can be prepared by a conventional method.
For example, an iodide compound represented by the following formula [II]:
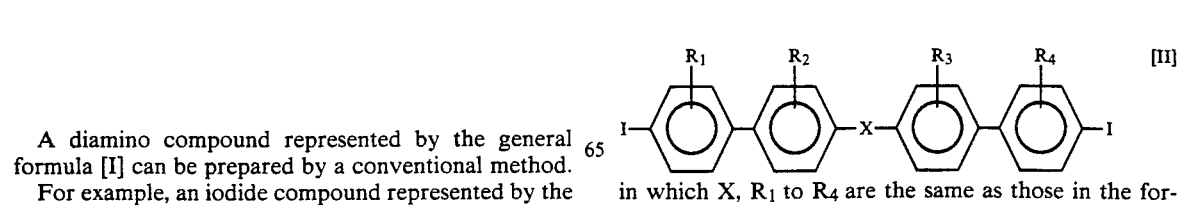
[II]
in which X, $R_1$ to $R_4$ are the same as those in the formula [I], is treated with amine compounds represented by the following general formulas [III] and [IV]:

   [III]

   [IV]

in which Ar₁ to Ar₄ are the same as those in the formula [I],
in an adequate solvent in the presence of a catalyst such as a basic compound or a transition metal compound according to Ullmann reaction to prepare a diamino compound of the present invention.

The diamino compound may be also prepared by treating a diamine compound represented by the following formula [V]:

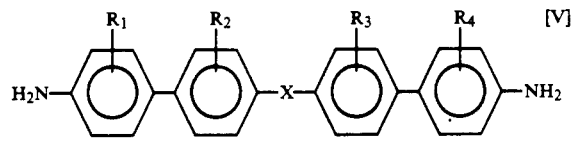   [V]

in which X, R₁ to R₄ are the same as those in the formula [I],
with iodine compounds represented by the following general formulas [VI], [VII], [VIII] and [IX]:

$$Ar_1—I \quad [VI]$$
$$Ar_3—I \quad [VII]$$
$$Ar_2—I \quad [VIII]$$
$$Ar_4—I \quad [IX]$$

in which Ar₁ to Ar₄ are the same as those in the formula [I],
in an adequate solvent in the presence of a catalyst such as a basic compound or a transition metal compound according to Ullmann reaction.

In another procedure, a compound represented by the general formula [V] is once acetylated and then condensed with iodide compounds of [VI] and [VII], followed by deacetylation of the obtained compound to be condensed with iodide compounds of [VIII] and [IX]

As to the basic compounds for the synthesis of a diamino compound of the present invention, alkali metal hydroxide, alkali metal carbonate, alkali metal bicarbonate and alkali metal alkolate are generally used. A quaternary ammonium compound and an organic base such as an aliphatic amine and an aromatic amine can be also used. Among these compounds, carbonates or bicarbonates of alkali metal or quaternary ammonium are preferable. The carbonates or bicarbonates of alkali metal are most preferable from viewpoints of reaction rate and heat stability.

As to the transition metals or transition compounds for the synthesis of a diamino compound of the present invention, metals such as Cu, Fe, Co, Ni, Cr, V, Pd, Pt and Ag and compounds thereof are used. Copper, palladium and compounds thereof are preferable from the viewpoint of yield. As to copper compounds, almost all copper compounds known may be used without limitation. Preferable ones are exemplified by CuI, CuCl, Cu₂O, CuBr, CuCN, Cu₂SO₄, CuSO₄, CuCl₂, Cu(OH)₂, CuO, CuBr₂, Cu₃(PO₄)₂, CuNO₃, Cu(NO₃)₂, CuCO₃, Cu(OCOCH₃), Cu(OCOCH₃)₂. Among those, CuCl, CuCl₂, CuBr, CuBr₂, CuI, CuO, Cu₂O, CuSO₄, Cu(OCOCH₃)₂ are preferable because of easy availability in the market. As to palladium compounds, halides, sulfates, nitrates and organic acid salts may be used. The usage of transition metals or transition compounds is 0.5–500 mole % on the basis of halide compound used in the reaction.

The solvents used in the reaction may be the ones known, preferably aprotic polar solvents such as nitrobenzene, dimethylformamide, dimethyl sulfoxide and N-methylpyrrolidone.

The reaction is carried out at 100°–250° C. under normal pressure or under pressure. After reaction, the solids deposited in the reaction solution are taken out and the solvent is removed to give diamino compound products.

The obtained amino compounds may be used singly or in mixture.

The diamino compound represented by the general formula [I] may be applied to a photosensitive member as a photosensitive material and is particularly useful as a charge transporting material. The diamino compound may be applied to a charge transporting layer of an electroluminescence device by taking advantage of its charge transportability.

First, it is explained hereinafter that the diamino compound represented by the general formula [I] is applied as a charge transporting material for a photosensitive member.

A photosensitive member of the present invention has a photosensitive layer containing one or more diamino compounds represented by the general formula [I]. A photosensitive member composed the diamino compound represented by the general formula [I] is excellent in sensitivity, charge trasportabily, initial surface potential and dark decreasing ratio and resistivity to light fatigue caused by repetition use.

There are known various forms of photosensitive member. The diamino compound of the present invention may be applied to any form of photosensitive member. For example, there is known a monolayer type in which a photosensitive layer containing a charge generating material and a charge transporting material dispersed in a binder resin is formed on an electrically conductive substrate and a laminated type in which a charge generating layer containing a charge generating material is formed on an substrate, followed by formation of a charge transporting layer on the charge generating layer. One or more of the diamino compounds of the present invention are used as a charge transporting material.

The diamino compound works as a charge transporting material in a photosensitive member and is able to carry very effectively electrical charges given by charge generating materials by light-absorption.

The diamino compound of the present invention is excellent in stability to light. As the compound does not have a double bond, it is hardly oxidized and excellent in ozone resistance. Therefore, a photosensitive member excellent in repetition durability can be obtained.

Moreover, the diamino compound of the present invention has good compatibility with a binder resin, resulting in rare deposition of crystals and contribution to improvement of sensitivity and repetition properties. A charge generating material useful for the present photosensitive member is exemplified by organic substances such as bisazo pigments, triarylmethane dyes, thiazine dyes, oxazine dyes, xanthene dyes, cyanine coloring agents, styryl coloring agents, pyrylium dyes, azo pigments, quinacridone pigments, indigo pigments, perylene pigments, polycyclic quinone pigments, bisbenzimidazole pigments, indanthrone pigments, squalylium pigments, azulene coloring agents phthalocyanine pigments, and pyrrlo-pyrrole pigments; and inorganic substances such as selenium, selenium-tellurium, selenium arsenic, cadmium sulfide, cadmium selenide, zinc oxide and amorphous silicon. Any other material is also usable insofar as it generates charge carriers very efficiently upon absorption of light.

The binder resins used for forming a photosensitive layer are exemplified with no significance in restricting the embodiments of the invention by thermoplastic resins such as saturated polyesters, polyamides, acrylic resins, ethylene-vinyl acetate copolymers, ion cross-linked olefin copolymers (ionomer), styrene-butadiene block copolymers, polycarbonates, vinyl chloride-vinyl acetate copolymers, cellulose esters, polyimides and styrols; thermosetting resins such as epoxy resins, urethane resins, silicone resins, phenolic resins, melamine resins, xylene resins, alkyd resins and thermosetting acrylic resins; photocuring resins; and photoconductive resins such as poly vinyl carbazole, polyvinyl pyrene, polyvinyl anthracene, polyvinylpyrrole. Any of these resins can be used singly or in combination with other resins. It is desirable for any of these electrically insulating resins to have a volume resistance of $1 \times 10^{12}$ $\Omega$cm or more when measured singly. In order to form a photosensitive member of a monolayer type, fine particles of a charge generating material are dispersed in a resin solution or a solution containing a charge transporting material and a binder resin and then the solution is sprayed on an electrically conductive substrate followed by drying. A thickness of the photosensitive layer is 3–50 $\mu$m, preferably 5–30 $\mu$m. The sensitivity becomes poor if the charge generating material is used in an insufficient quantity, whereas the chargeability becomes poor and the mechanical strength of photosensitive layer is inadequate if used to excess. Therefore, the amount of the charge generating material is within the range of 0.01–2 parts by weight, preferably 0.2–1.2 parts by weight on the basis of one part by weight of the binder resin of the photosensitive layer. The amount of diamino compound of the formula [I] as a charge transporting material is within the range of 0.01–2 parts by weight, preferably 0.2–1.5 parts by weight. on the basis of one part by weight of the binder resin. If the amount is less than 0.01 part by weight, sensitivity becomes poor. If the amount is more than 2 parts by weight, mechanical strength of the photosensitive layer and repetition properties become poor.

In order to form a photosensitive member of a laminated type, a charge generating material is deposited in a vacuum on an electrically conductive substrate, a charge generating material is dissolved in an adequate solvent to apply onto an electrically conductive substrate or an application solution containing a charge transporting material and, if necessary, a binder resin dissolved in an appropriate solvent is applied onto an electrically conductive substrate to be dried, for the formation of a charge generating layer on an electrically substrate. Then, a solution containing a charge transporting material and a binder resin is applied onto the charge generating layer followed by drying for the formation of a charge transporting layer. A thickness of the charge generating layer is 4 $\mu$m or less, preferably 2 $\mu$m or less. A thickness of the charge transporting layer is 3–50 $\mu$m, preferably 5–30 $\mu$m. A ratio of the charge transporting material in the charge transporting layer is 0.2–2 parts by weight, preferably 0.3–1.3 parts by weight on the basis of one part by weight of the binder resin.

A photosensitive member of the present invention permits, in combination with the binder, the use of a plasticizer such as halogenated paraffin, polybiphenyl chloride, dimethyl naphthalene, dibuthyl phthalate and o-terphenyl, the use of an electron-attracting sensitizer such as chloranyl, tetracyanoethylene, 2,4,7-trinitrofluorenone, 5,6-dicyanobenzoquinone, tetracyanoquinodimethane, tetrachlorophthalic anhydride and 3,5-dinitrobenzoic acid, or the use of a sensitizer such as methyl violet, rhodamine B, cyanine dye, pyrylium salt and thiapyrylium salt.

An electrically conductive substrate is exemplified by a sheet or a drum made of metal or alloy such as copper, aluminum, silver, iron and nickel; a substrate such as a plastic film on which the foregoing metal or alloy is adhered by a vacuum-deposition method or an electroless plating method and the like; substrate such as a plastic film and paper on which an electro-conductive layer is formed by applying or depositing electroconductive polymer, indium oxide, tin oxide etc.

Concrete constitutions of a photosensitive member are shown in FIG. 1 to FIG. 5.

FIG. 1 shows a monolayer type in which a photosensitive layer (4) containing a charge generating material (3) and a charge transporting material (2) dispersed in a binder resin is formed on an electrically conductive substrate. The diamino compound of the present invention is used as the charge transporting material.

Figure 2:
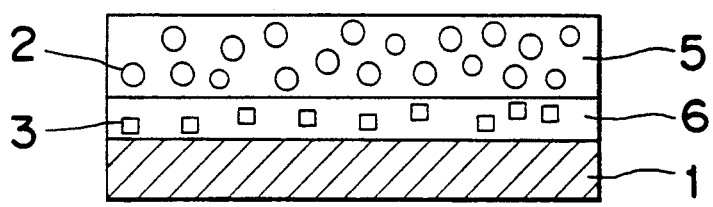
FIG. 2 is a schematic sectional view of a function-divided photosensitive member having a charge generating layer and a charge transporting layer on an electrically conductive substrate in this order.

FIG. 2. shows a function-divided type in which a photosensitive layer is composed of a charge generating layer (6) and a charge transporting layer (5). The charge transporting layer (5) is formed on the surface of the charge generating layer (6). The diamino compound of the present invention is incorporated into the charge transporting layer (5).

Figure 3:
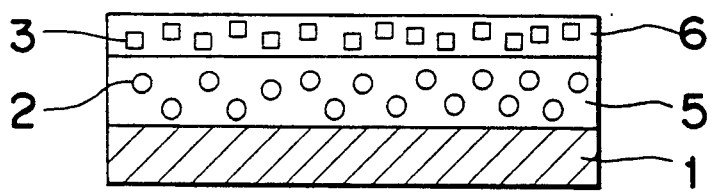
FIG. 3 is a schematic sectional view of a function-divided photosensitive member having a charge transporting layer and a charge generating layer on an electrically conductive substrate in this order.

A photosensitive member shown in FIG. 3 is similar to that of FIG. 2 in a function divided type having a charge generating layer (6) and a charge transporting layer (5), but different in that the charge generating layer (6) is formed on the surface of the charge transporting layer (5).

Figure 4:
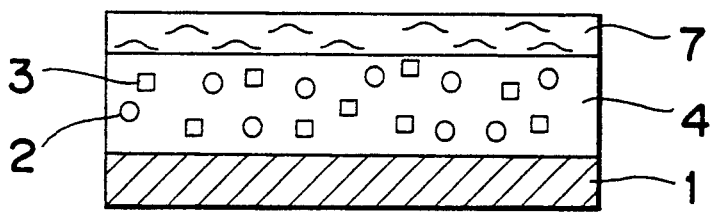
FIG. 4 is a schematic sectional view of a photosensitive member having a photosensitive layer and a surface protective layer on an electrically conductive substrate in this order.

A photosensitive member shown in FIG. 4 has further a surface protective layer (4) formed on the photosensitive member of FIG. 1. The photosensitive layer (7) may be a function divided type having a charge generating layer (6) and a charge transporting layer (5).

Figure 5:
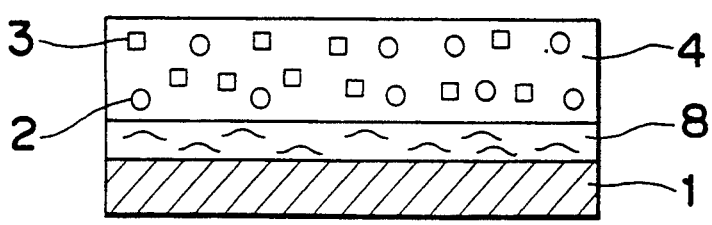
FIG. 5 is a schematic sectional view of a photosensitive member having an intermediate layer and a photosensitive layer on an electrically conductive substrate in this order.

A photosensitive member shown in FIG. 5 has an intermediate layer between a substrate (1) and a photosensitive layer (4). The intermediate layer is effective in improvement of adhesivity, improvement of coatability, protection of the substrate, improvement of charge injection from the substrate into the photosensitive layer.

Materials used for the formation of the intermediate layer is exemplified by polyimides, polyamides, nitrocelluloses, polyvinyl butyrals, polyvinyl alcohols and aluminum oxide. It is desirable that a thickness of the intermediate layer is 1 μm or less.

A diamino compound of the present invention represented by the general formula [I] can be applied to a charge transporting layer of an electroluminescent device by taking advantage of its charge transporting properties. The application of the diamino compound of the present invention to an electroluminescent device is explained hereinafter.

An electroluminescent device is composed of at least an organic luminous layer and a charge transporting layer between electrodes.

Figure 6:
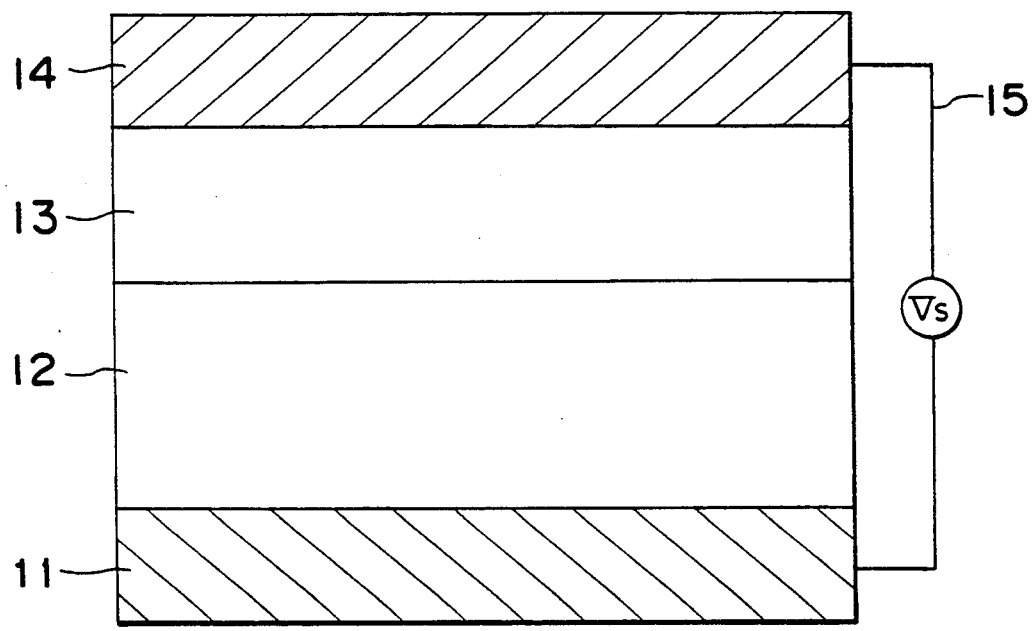
FIG. 6 is a schematic sectional view of an electroluminescence device.

A sectional schematic view of an electroluminescent device is shown in FIG. 6. In the figure, the reference number (11) is an anode, on which a charge transporting layer (12), an organic luminous layer (13) and a cathode (14) are laminated in the order. A a diamino compound of the present invention represented by the general formula [I] is contained in the charge transporting layer.

A voltage is applied between the anode (11) and the cathode (14) to give luminescence.

As to an electrically conductive material used as the anode (11) of the organic electroluminescent device, the ones having work function of 4 eV or more are preferable and exemplified by carbon, aluminum, vanadium, iron, cobalt, nickel, copper, zinc, tungsten, silver, tin, gold, alloy thereof, tin oxide and indium oxide.

As to an electrically conductive material used as the cathode (14) of the organic electroluminescent device, the ones having working function of 4 eV or less and exemplified by magnesium, calcium, titanium, yttrium, lithium, gadolinium, ytterbium, ruthenium, manganese and an alloy thereof.

In the organic electroluminescent device, at least one of the anode (11) or the cathode (14) is made transparent so that luminescence can be seen. A transparent electrode is formed by depositing or sputtering electroconductive materials above mentioned on a transparent substrate to give a desired transparency. The transparent substrate is not particularly limited so far as it has an adequate strength and is not influenced adversely by heat generated in deposition process during the preparation of an electroluminescence device. Such a transparent material is exemplified by a glass substrate, transparent resin such as polyethylene, polypropylene, polyether-sulfone, poly-ether-ether-ketone.

A transparent electrode available in the market such as ITO and NESA is known in which a transparent electrode is formed on a glass substrate.

The charge transporting layer (12) may be formed by depositing a diamino compound represented by the general formula [I] or spin-coating an adequate resin-solution of the diamino compound.

When the charge transporting layer (12) is formed by a deposition method, its thickness is 0.01-0.3 μm in general. When the charge transporting layer (12) is formed by a spin-coating method, its thickness is 0.05-1.0 μm and the diamino compound is incorporated at a content of 20-80% by weight on the basis of a binder resin.

Then, an organic luminous layer is formed on the charge transporting layer (12).

As to organic luminous materials incorporated in the organic luminous layer, the ones known can be used and exemplified by epitolidine, 2,5-bis[5,7-di-t-pentyl-2-benzoxazolyl]thiophene, 2,2'-(1,4-phenylenedivinylene)bisbenzothiazole, 2,2'-(4,4'-biphenylene)bisbenzothiazole, 5-methyl-2-{2-[4-(5-methyl-2-benzoxazolyl)phenyl]-vinyl}benzoxazole, 2,5-bis(5-methyl-2-benzoxazolyl)-thiophene, anthracene, naphthalene, phenanthrene, pyrene, chrysene, perylene, perylenequinone, 1,4-diphenylbutadiene, tetraphenylbutadiene, coumarin, acridine stilbene, 2-(4-biphenyl)-6-phenylbenzoxazole, aluminum trioxine, magnesium bisoxine, zinc bis(benzo-8-qunolinol), bis(2-methyl-8-qunolinolate)aluminum oxide, indium trisoxine, aluminum tris(5-methyloxine), lithium oxine, gallium trioxine, calcium bis(5-chloroxine), poly-zinc-bis(8-hydroxy-5-qunolinyl)methane), dilithium epindridione, zinc bisoxine, 1,2-phthaloperynone and 1,2-naphthaloperynone. Further, general fluorescent dyes such as fluorescent coumarin dyes, fluorescent perylene dyes, fluorescent pyran dyes, fluorescent thiopyran dyes, fluorescent polymethine, fluorescent merocyanine dyes and fluorescent imidazole dyes. Particularly preferable ones are chelated oxinoides.

The organic luminous layer may be a monolayer type formed with the above mentioned luminous compounds or may be a multilayer type in order to adjust color of luminescence, strength of luminescence and the like.

Finally, a cathode is formed on the organic luminous layer, so that an organic luminescent device in which the charge transporting layer(12), the luminous layer (13) and the cathode (14) are laminated on the anode(11) in the order is obtained. The charge transporting layer (12) and the luminous layer (13) may be formed on the cathode (14) in the order.

A pair of transparent electrodes are bonded to an adequate lead wire such as nichrome wire, gold wire, copper wire and platinum wire and a voltage is applied to the electrodes so that luminant light may be given.

An organic electroluminescence device can be applied to various kinds of display devices.

Specific examples are shown below. In the examples, the wording "part(s)" means "part(s) by weight" so far as it is not explained particularly.

SYNTHETIC EXAMPLE 1

Synthetic Example of the Diamino Compound [15]

The iodide compound represented by the following formula:

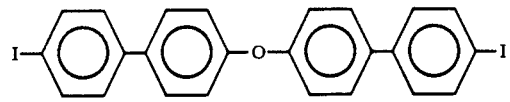

of 5.7 g, 4,4'-ditolylamine of 4.7 g, potassium carbonate of 3.5 g, copper powder of 1 g and nitrobenzene of 50 g were placed in a four-necked flask of 200 ml capacity with a reflux condenser to be treated for 24 hours at 200° C. under nitrogen stream.

After reaction, nitrobenzene was removed by means of a steam distillation method. Then, tetrahydrofuran of 100 g was added to the reaction solution and solids were filtrated. The filtrate was subjected to silica gel column chromatography. The separated products were purified by recrystallization from toluene-ethanol solvent to give white crystals of 5.0 g. The result of elemental analysis of the resultant ($C_{48}H_{44}N_2O$) is shown in Table 1 below.

TABLE 1

|  | C (%) | H (%) | N (%) |
|---|---|---|---|
| calculated | 86.75 | 6.63 | 4.22 |

TABLE 1-continued

| | C (%) | H (%) | N (%) |
|---|---|---|---|
| found | 86.72 | 6.59 | 4.18 |

EXAMPLE 1

The bisazo compound (0.45 parts) represented by the general formula [A] below:

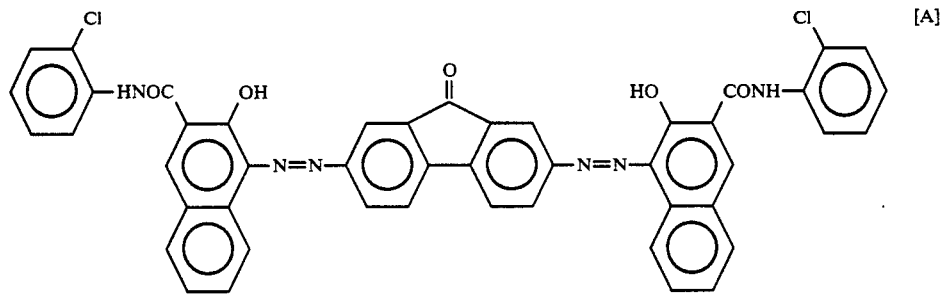

polyester resin (Vylon 200; made by Toyobo K.K.) of 0.45 parts and cyclohexanone of 50 parts were placed in Sand grinder for dispersion. The dispersion solution of the bisazo compound was applied onto aluminotype-Mylar of 100 micron thickness by film applicator to form a charge generating layer so that the thickness of dried layer would be 0.3 g/m².

A solution containing the diamino compound [2] of 70 parts and polycarbonate resin (Panlite K-1300, made by Teijin Kasei K.K.) of 70 parts dissolved in 1,4-dioxane of 400 parts was applied onto the charge generating layer to form a charge transporting layer so that the thickness of dried layer would be 16 microns. Thus, a photosensitive member with two layers was prepared.

The resultant photosensitive member was installed in a copying machine (EP-470Z; made by Minolta Camera K.K.) and corona-charged by power of −6 KV level to evaluate initial surface potential $V_0$ (V), half-reducing amount ($E_{\frac{1}{2}}$ (lux.sec)) and dark decreasing ratio of the initial surface potential ($DDR_1$). $E_{\frac{1}{2}}$ means an exposure amount required to reduce the initial surface potential to half the value. $DDR_1$ is a decreasing ratio of the initial surface potential after the photosensitive member was left for 1 second in the dark.

EXAMPLES 2-4

Photosensitive members were prepared in a manner similar to Example 1 except that the diamino compounds [3], [4] and [5] were used respectively instead of the diamino compound [2].

$V_0$, $E_{\frac{1}{2}}$ and $DDR_1$ were evaluated on the obtained photosensitive members in a manner similar to Example 1.

EXAMPLE 5

The bisazo compound (0.45 parts) represented by the general formula [B] below:

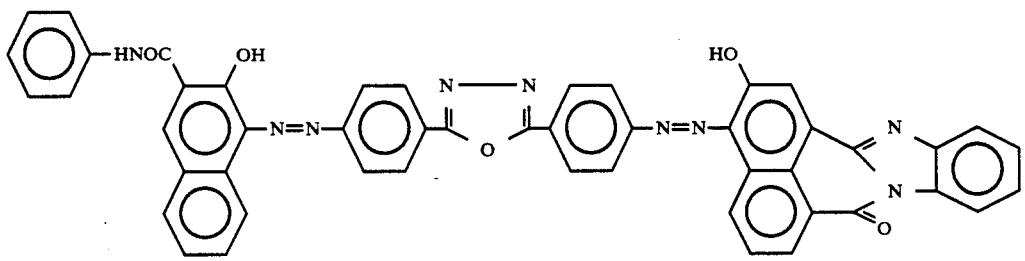

polystyrene resin (molecular weight of 40,000) of 0.45 parts and cyclohexanone of 50 parts were placed in Sand grinder for dispersion.

The dispersion solution containing the bisazo compound was applied onto aluminotype-Mylar of 100 micron thickness by film applicator to form a charge generating layer so that the thickness of dried layer would be 0.3 g/m².

A solution containing the diamino compound [7] of 70 parts and polyarylate resin (U-100; made by Yunichica K.K.) of 70 parts dissolved in 1,4-dioxane of 400 parts was applied onto the charge generating layer to form a charge transporting layer so that the thickness of dried layer would be 16 microns. Thus, a photosensitive member with two layers was prepared.

$V_0$, $E_{\frac{1}{2}}$ and $DDR_1$ were evaluated on the obtained photosensitive members in a manner similar to Example 1.

EXAMPLE 6-8

Photosensitive members were prepared in a manner similar to Example 5 except that the diamino compounds [11], [12] and [13] were respectively used instead of the diamino compound [7].

$V_0$, $E_{\frac{1}{2}}$ and $DDR_1$ were evaluated on the obtained photosensitive members in a manner similar to Example 1.

EXAMPLE 9

The polycyclic quinone compound (0.45 parts) represented by the general formula [C] below:

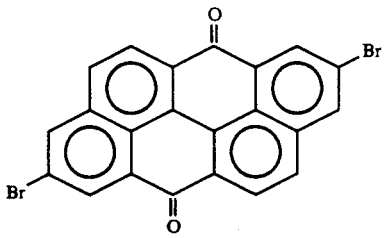

[C]

polycarbonate resin (Panlite K-1300; made by Teijin Kasei K.K.) of 0.45 parts and dicloroethane of 50 parts were placed in Sand grinder for dispersion. The dispersion solution of the polycyclic quinone pigments was applied onto aluminotype-Mylar of 100 micron thickness by film applicator to form a charge generating layer so that the thickness of dried layer would be 0.4 $g/m^2$.

A solution containing of the diamino compound [16] of 60 parts and polyarylate resin (U-100; made by Yunichica K.K.) of 50 parts dissolved in 1,4-dioxane of 400 parts was applied onto the charge generating layer to form a charge transporting layer so that the thickness of dried layer would be 18 microns. Thus, a photosensitive member with two layers was prepared.

$V_0$, $E_{\frac{1}{2}}$ and $DDR_1$ were evaluated on the obtained photosensitive members in a manner similar to Example 1.

EXAMPLES 10-11

Photosensitive members were prepared in a manner similar to Example 9 except that the diamino compounds [17] and [21] were respectively used instead of the diamino compound [16].

$V_0$, $E_{\frac{1}{2}}$ and $DDR_1$ were evaluated on the obtained photosensitive members in a manner similar to Example 1.

EXAMPLE 12

The perylene pigments (0.45 parts) represented by the general formula [D] below:

$V_0$, $E_{\frac{1}{2}}$ and $DDR_1$ were evaluated on the obtained photosensitive member in a manner similar to Example 1.

EXAMPLES 13-14

Photosensitive members were prepared in a manner similar to Example 12 except that the diamino compounds [23] and [24] were used respectively instead of the diamino compound [22].

$V_0$, $E_{\frac{1}{2}}$ and $DDR_1$ were evaluated on the obtained photosensitive members in a manner similar to Example 1.

EXAMPLE 15

Titanylphthalocyanine of 0.45 parts, butyral resin (BX-1; made by Sekisui Kagaku Kogyo K.K.) of 0.45 parts and dicloroethane of 50 parts were placed in Sand grinder for dispersion.

The dispersion solution of the phthalocyanine pigment was applied onto aluminotype-Mylar of 100 micron thickness by film applicator to form a charge generating layer so that the thickness of dried layer would be 0.3 $g/m^2$.

A solution containing the diamino compound [25] of 50 parts and polycarbonate resin (PC-Z; made by Mitsubishi Gas Kagaku K.K.) of 50 parts dissolved in 1,4-dioxane of 400 parts was applied onto the charge generating layer to form a charge transporting layer so that the thickness of dried layer would be 18 microns. Thus, a photosensitive member with two layers was prepared.

$V_0$, $E_{\frac{1}{2}}$ and $DDR_1$ were evaluated on the obtained photosensitive members in a manner similar to Example 1.

EXAMPLES 16 AND 17

Photosensitive members were prepared in a manner similar to Example 15 except that the diamino compounds [27] and [32] were used respectively instead of the diamino compound [25].

$V_0$, $E_{\frac{1}{2}}$ and $DDR_1$ were evaluated on the obtained photosensitive member in a manner similar to Example 1.

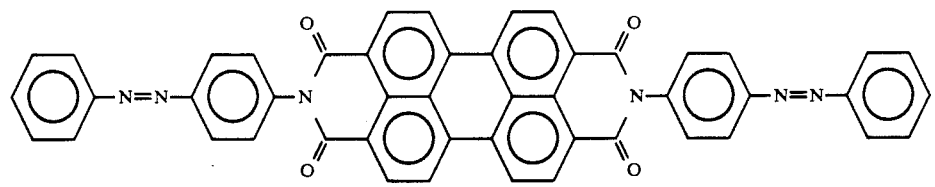

[D]

butyral resin (BX-1; made by Sekisui Kagaku Kogyo K.K.) of 0.45 parts and dicloroethane of 50 parts were placed in Sand grinder for dispersion.

The dispersion solution of the perylene pigment was applied onto aluminotype-Mylar of 100 micron thickness by film applicator to form a charge generating layer so that the thickness of dried layer would be 0.4 $g/m^2$.

A solution containing the diamino compound [22] of 50 parts and polycarbonate resin (PC-Z; made by Mitsubishi Gas Kagaku K.K.) of 50 parts dissolved in 1,4-dioxane of 400 parts was applied onto the charge generating layer to form a charge transporting layer so that the thickness of dried layer would be 18 microns. Thus, a photosensitive member with two layers was prepared.

EXAMPLE 18

Copper phthalocyanine of 50 parts and tetranitrocopper phthalocyanine of 0.2 parts were dissolved in 98% conc. sulfuric acid of 500 parts with stirring. The solution was poured into water of 5000 parts to deposit a photoconductive composition of copper phthalocyanine and tetranitro-copper phthalocyanine. The obtained composition was filtered, washed and dried at 120° C. under vacuum conditions.

The photoconductive composition obtained above of 10 parts, thermosetting acrylic resin (Acrydick A405; made by Dainippon Ink K.K.) of 22.5 parts, melamine resin (Super Beckamine J820; made by Dainippon Ink K.K.) of 7.5 parts, the diamino compound [3] of 15 parts and mixed solution of methyl ethyl ketone and xylene (1:1) of 100 parts were placed in a ball mill pot for dispersion. The mixture was mixed for dispersion for 48 hours to give a photosensitive application solution. The application solution is applied onto an aluminum substrate and dried. Thus, a photosensitive layer having thickness of 15 microns was formed.

$V_0$, $E_{\frac{1}{2}}$ and $DDR_1$ were evaluated on the obtained photosensitive member in a manner similar to Example 1 except that the photosensitive member was corona-charged by power of +6 KV level.

EXAMPLES 19-21

Photosensitive members were prepared in a manner similar to Example 18 except that the diamino compounds [15], [23] and [33] were respectively used instead of the diamino compound [3].

$V_0$, $E_{\frac{1}{2}}$ and $DDR_1$ were evaluated on the obtained photosensitive members in a manner similar to Example 18.

COMPARATIVE EXAMPLES 1-4

Photosensitive members were prepared in a manner similar to Example 18 except that the compounds represented by the formulas [E], [F], [G] and [H] were respectively used instead of the diamino compound [3].

$V_0$, $E_{\frac{1}{2}}$ and $DDR_1$ were evaluated on the obtained photosensitive members in a manner similar to Example 18.

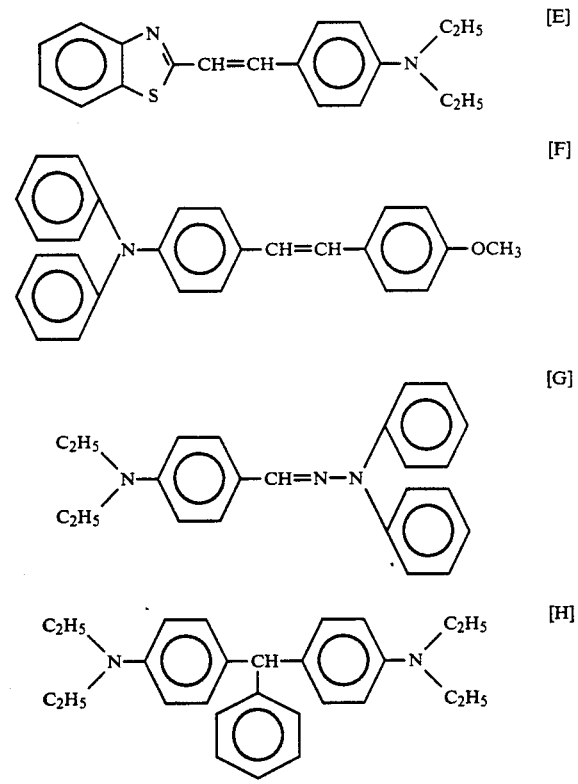

COMPARATIVE EXAMPLES 5-7

Photosensitive members were prepared in a manner similar to Example 18 except that the compounds represented by the following formulas [I], [J] and [K] were respectively used instead of the diamino compound [3].

$V_0$, $E_{\frac{1}{2}}$ and $DDR_1$ were evaluated on the obtained photosensitive members in a manner similar to Example 1.

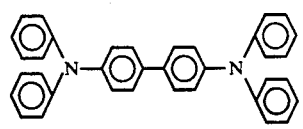

[I]

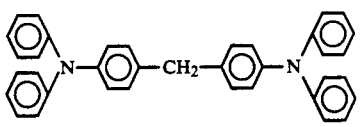

[J]

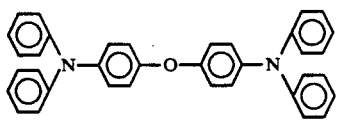

[K]

In Comparative Examples 1-7, it was observed that some crystals were deposited partially when the photosensitive layers were formed with the use of photosensitive application solution containing the compounds of [G], [H] and [I].

The results of $V_0$, $E_{\frac{1}{2}}$ and $DDR_1$ with respect to the photosensitive members obtained Examples 1-21 and Comparative Examples 1-7 were summarized in Table 2 below.

TABLE 2

|  | $V_0$ (V) | $E_{\frac{1}{2}}$ (lux·sec) | $DDR_1$ (%) |
| --- | --- | --- | --- |
| Example 1 | −650 | 1.2 | 3.1 |
| Example 2 | −660 | 1.0 | 2.7 |
| Example 3 | −650 | 0.8 | 3.0 |
| Example 4 | −650 | 0.9 | 2.9 |
| Example 5 | −650 | 1.0 | 2.9 |
| Example 6 | −640 | 1.2 | 3.5 |
| Example 7 | −650 | 1.1 | 3.1 |
| Example 8 | −650 | 1.0 | 3.0 |
| Example 9 | −640 | 0.8 | 3.4 |
| Example 10 | −650 | 1.2 | 2.8 |
| Example 11 | −650 | 1.1 | 2.9 |
| Example 12 | −660 | 1.0 | 2.4 |
| Example 13 | −650 | 1.3 | 2.8 |
| Example 14 | −660 | 1.3 | 2.6 |
| Example 15 | −650 | 1.1 | 3.0 |
| Example 16 | −660 | 1.3 | 2.6 |
| Example 17 | −650 | 1.2 | 2.9 |
| Example 18 | +620 | 0.9 | 12.3 |
| Example 19 | +610 | 0.8 | 13.0 |
| Example 20 | +600 | 1.0 | 13.2 |
| Example 21 | +610 | 0.8 | 12.8 |
| Comp. Example 1 | +620 | 15.0 | 12.0 |
| Comp. Example 2 | +600 | 6.5 | 13.7 |
| Comp. Example 3 | +600 | 3.2 | 14.3 |
| Comp. Example 4 | +620 | 13.5 | 10.4 |
| Comp. Example 5 | +620 | 3.0 | 11.6 |
| Comp. Example 6 | +630 | 5.4 | 10.2 |
| Comp. Example 7 | +630 | 5.9 | 10.1 |

It is understood from Table 1 that the photosensitive members of the present invention, even though they are laminated types or monolayer-types, have sufficient charge keeping ability, low dark decreasing ratio such that the photosensitive members can be taken into practical use and excellent sensitivity.

Further, the photosensitive members of Example 18 was respectively installed into a copying machine (EP-350Z; made by Minolta Camera K.K.) to be subjected to positively charged repetition test. Even after 1000 times of copy, clear copy images excellent in gradation were formed both at initial stage and final stage through the test and the sensitivity was stable. Accordingly, the photosensitive members of the present invention were also excellent in repetition properties.

What is claimed is:

1. A photosensitive member having a photosensitive layer on an electrically conductive substrate, characterized by that the photosensitive layer comprises a diamino compound represented by the following general formula [I]:

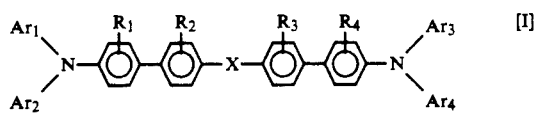

in which $Ar_1$, $Ar_2$, $Ar_3$ and $Ar_4$ represent respectively an alkyl group, an aralkyl group, an aryl group, a biphenyl group or a heterocyclic group, each of which may have a substituent; $R_1$, $R_2$, $R_3$ and $R_4$ represent respectively a hydrogen atom, an alkyl group, an alkoxy group or a halogen atom; X represents —O—, —S— or

in which $R_5$ and $R_6$ represent respectively a hydrogen atom, an alkyl group or an aryl group.

2. A photosensitive member of claim 1, in which the photosensitive layer further comprises a resin and a charge generating material.

3. A photosensitive member of claim 2, in which the photosensitive layer contains the charge generating material at a content of 0.01 to 2 parts by weight on the basis of 1 part by weight of resin.

4. A photosensitive member of claim 1, in which the photosensitive layer has a thickness of 3–50 μm.

5. A photosensitive member of claim 1, in which the photosensitive layer comprises a charge generating layer and a charge transporting layer.

6. A photosensitive member of claim 5, in which the charge generating layer has a thickness of 4 μm or less.

7. A photosensitive member of claim 5, in which the charge transporting layer has a thickness of 3 to 50 μm.

8. A photosensitive member of claim 5, in which the charge transporting layer contains the diamino compound at a content of 0.2 to 2 parts by weight on the basis of 1 part by weight of a binder resin.

9. A photosensitive member of claim 1, in which at least one of the $Ar_1$ to $Ar_4$ is a phenyl group or a biphenyl group, each of which may have a substituent.

* * * * *